United States Patent
Antkowiak et al.

(10) Patent No.: US 7,810,927 B2
(45) Date of Patent: Oct. 12, 2010

(54) REFRACTIVE TREATMENT DEVICE WITH SLIT ILLUMINATION

(75) Inventors: Gerard Antkowiak, Jena (DE); Marco Hanft, Jena (DE); Elke Ebert, Jena (DE); Karsten Festag, Jena (DE); Juergen Ledermann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 417 days.

(21) Appl. No.: 11/937,162

(22) Filed: Nov. 8, 2007

(65) Prior Publication Data

US 2008/0123051 A1 May 29, 2008

(30) Foreign Application Priority Data

Nov. 10, 2006 (DE) .................. 10 2006 053 581

(51) Int. Cl.
*A61B 3/10* (2006.01)

(52) U.S. Cl. ............... 351/214; 351/221; 351/205

(58) Field of Classification Search ........... 351/214, 351/213, 221, 205, 246, 247, 211, 212
See application file for complete search history.

(56) References Cited

U.S. PATENT DOCUMENTS

| 4,315,672 | A | * | 2/1982 | Muller et al. | ............... 351/212 |
|---|---|---|---|---|---|
| 5,562,656 | A | * | 10/1996 | Sumiya | ............... 606/4 |
| 6,382,794 | B1 | | 5/2002 | Lai et al. | |
| 6,409,346 | B1 | | 6/2002 | Koest et al. | |

FOREIGN PATENT DOCUMENTS

DE 299 13 603 U1 12/1999

OTHER PUBLICATIONS

Excimer-Laser MEL 80. Prospectus 000000-1382-096 of Carl Zeiss Meditec AG. 2005.[online]URL:<http://www.meditec.zeiss.de/88256DE40004A9B4/0/83F962277FA3ADCB882572270000A6F5/file/mel80_de.pdfl>[recherchiert Oct. 29, 2007].

\* cited by examiner

*Primary Examiner*—Hung X Dang
(74) *Attorney, Agent, or Firm*—Patterson Thuente Christensen Pedersen, PA

(57) ABSTRACT

A solution by which an examination of the cornea for possible encapsulations, air bubbles, or other irregularities following a refractive surgery can be carried out directly at the treatment device instead of the patient having to be transferred to an examination device.

The additional slit illumination system includes two slit projector units substantially symmetrically mounted at an angle of about 40° to the optical axis of the refractive treatment device, and fixed and focused on the eye of the patient to be examined. The slit projector units include a light source, a projection optical system, and beam forming and/or conducting optical components.

Although intended for surgical microscopes, it can also be used for other opthalmologic treatment devices that would benefit from a slit projection system for the examination before, during, or after the treatment procedure.

18 Claims, 2 Drawing Sheets

REFRACTIVE TREATMENT DEVICE WITH SLIT ILLUMINATION

RELATED APPLICATION

The present application claims the benefit of priority to German Patent Application No. 10 2006 53 581.2 filed on Nov. 10, 2006. Said application is incorporated by reference herein.

FIELD OF THE INVENTION

The invention at hand relates to a solution by which an examination of the cornea for possible encapsulations, air bubbles, or other irregularities following a refractive surgery can be carried out directly at the treatment device instead of the patient having to be transferred to an examination device.

BACKGROUND OF THE INVENTION

The examination of the optically transparent cornea requires a special lighting technique via an illuminated slit projected onto the eye.

The known state-of-the-art treatment devices, specifically refractive lasers for refractive surgeries on the eye, do not include these slit projection devices. Rather, it is common practice to examine the patient using an examination system at a separate location after completing the surgery. The disadvantage of this procedure is that the patient has to get up and that possible problems cannot be alleviated immediately on site with the surgical microscope.

Another known solution, as is being practiced on the refractive laser device MEL80 by Carl Zeiss Meditec AG, provides for the adaptation of a slit illumination projector on the treatment device which can be transported into several positions necessary for the procedure via a guide mechanism. The main disadvantage here is the patient's and operator's freedom of movement being limited by the guide mechanism. Furthermore, the operating field light must be switched off separately while the slit lamp illumination is being used.

Further disadvantages lie with the halogen lamps used as a state-of-the-art light source for the slit illumination—their short lifespan and high heat-radiation.

SUMMARY OF THE INVENTION

The invention at hand is based on the task of eliminating the disadvantages of the state-of-the-art and to provide a solution for a refractive treatment that allows an examination of the cornea directly on the treatment device without limiting the freedom of movement of the patient and the operator.

According to the invention, this task is solved by the functions of the independent claims. Preferred further developments and extended designs are the object of the dependent claims.

With the refractive treatment device with slit projection according to this invention for follow-up exams, the additional slit projection system consists of two slit projector units which are mounted at an angle of about 40° to the optical axis, symmetrical and fixed and focused on the eye of the patient. These units include a light source, a projection optical system, and beam forming and/or conducting optical components.

Although the proposed technical solution is intended specifically for refractive lasers, it can also be used for other opthalmologic treatment devices requiring a slit projection system for the examination before, during, or after the treatment procedure.

BRIEF DESCRIPTION OF THE DRAWINGS

The invention is described in further detail in the following example embodiments.

DETAILED DESCRIPTION

According to this invention the proposed refractive treatment device with slit projection for follow-up exams includes two additional slit projector units which are mounted fixed, symmetrical, and at an angle of about 40° to the optical axis and focused on the eye of the patient. They include a light source, a projection optical system, and beam forming and/or conducting optical components.

Contrary to the usual application of slit lamp units, the units proposed in this technical solution are located at a long working distance of 200 to 250 mm from the patient's eye.

The location of the slit projector units at an angle of about 40°, symmetrical to the optical axis, on an imaginary circular arc whose center point is located at the patient's eye, allows for oblique slit illumination of the eye to be examined from two different directions without the patient having to change positions. The necessary examinations can be performed directly beneath the surgical microscope.

Figure 1:
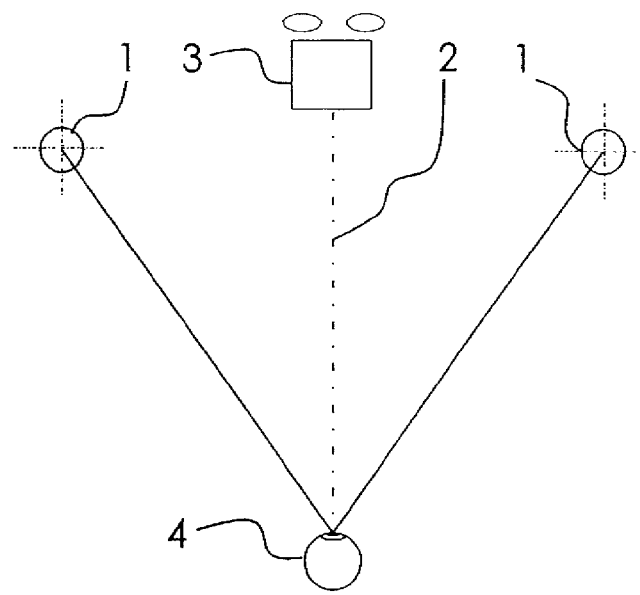
FIG. 1 is a schematic depiction of a basic arrangement of the solution according to the invention

FIG. 1 shows a basic arrangement of the solution according to the invention where the slit projector units, 1, are arranged at an angle of about 40°, symmetrical to the optical axis, 2, of the refractive treatment device, 3, and where the slit projector is focused on the eye to be examined, 4, from an angle.

The actual treatment beam is located on the optical axis, 2. It is generated by a laser source and pulsed and focused onto the surfaces of the eye, 4, to be treated. In a first example layout, laser sources with pulse durations in the femtosecond range with pulse repeat frequencies between 10 and 500 kHz are used.

In order to avoid the disadvantages of a halogen light source, LEDs featuring steplessly adjustable brightness are used as a light source for the slit projector units. To adapt the color temperature of the light beams to the color temperature of conventional halogen lamps, white LEDs with adjustable color filters featuring steplessly adjustable brightness can be used instead of warm white LEDs.

As the beam bundle emitted by LEDs is generally very divergent, beam forming and/or beam conducting optical components are arranged in front of the light source. These can include a spherical lens with a high numeric aperture. In addition, there is a slit aperture located in front of the light source to create a slit image, which can be 0.10 to 0.50 mm wide and 10 and 15 mm high. The preferred values are 0.25 mm and 12 mm.

For the precise movement of the slit image over the eye, the slit projector units are equipped with a control unit including a coaxial planetary gear with a respective control element.

Figure 2:
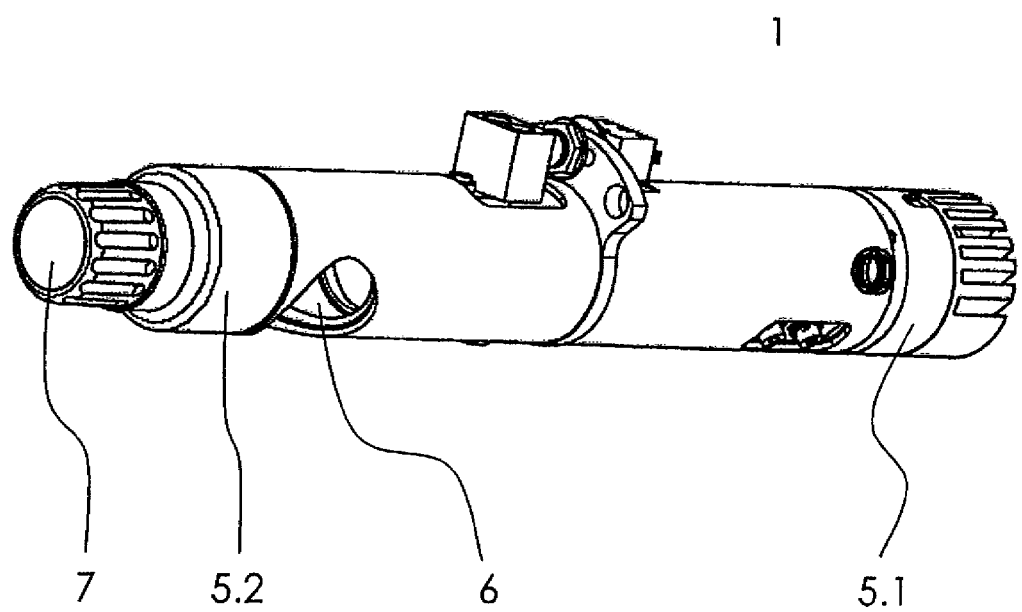
FIG. 2 is an external perspective view of a slit projector unit according to the invention.

The exterior view of the slit projection system according to this invention is depicted in FIG. 2. In this example depiction, the slit projection system according to this invention, 1, has a generally cylindrical exterior, whose front end, 5.1, is connected to the refractive treatment device (not shown). Front end, 5.1, of the slit projector unit, 1, contains the light source, which is connected to the power supply via the control unit of the refractive treatment device, 3. Beam forming and/or beam conducting optical components as well as a projection optical system are arranged on the beam in the generally cylindrical exterior in front of the light source. There is an opening, 6, in the exterior surface of the rear end, 5.2, of the generally cylindrical exterior, through which the slit image exits via a deflection mirror to be focused onto the eye to be examined, 4.

Finally, there is a control element, 7, located on the face of the rear end, 5.2, of the slit projector unit 1, which is used to move the slit image precisely across the eye, 4. The control element, 7, is connected to a coaxial planetary gear which is located inside the generally cylindrical exterior.

In an advantageous arrangement of the solution according to this invention the control unit in the refractive treatment device regulates an intelligent lighting regimen which involves the use of at least one of the lighting systems—either one of the slit projector units or the surgical field lighting system. After completion of the treatment, the slit projector unit is switched on which automatically switches off the surgical field lighting system. Even if there is a switch to the second slit projector unit, the first one is switched off. If there are no more slit projector units in operation the refractive treatment device is switched off or the surgical field lighting system is reactivated.

Figure 3:
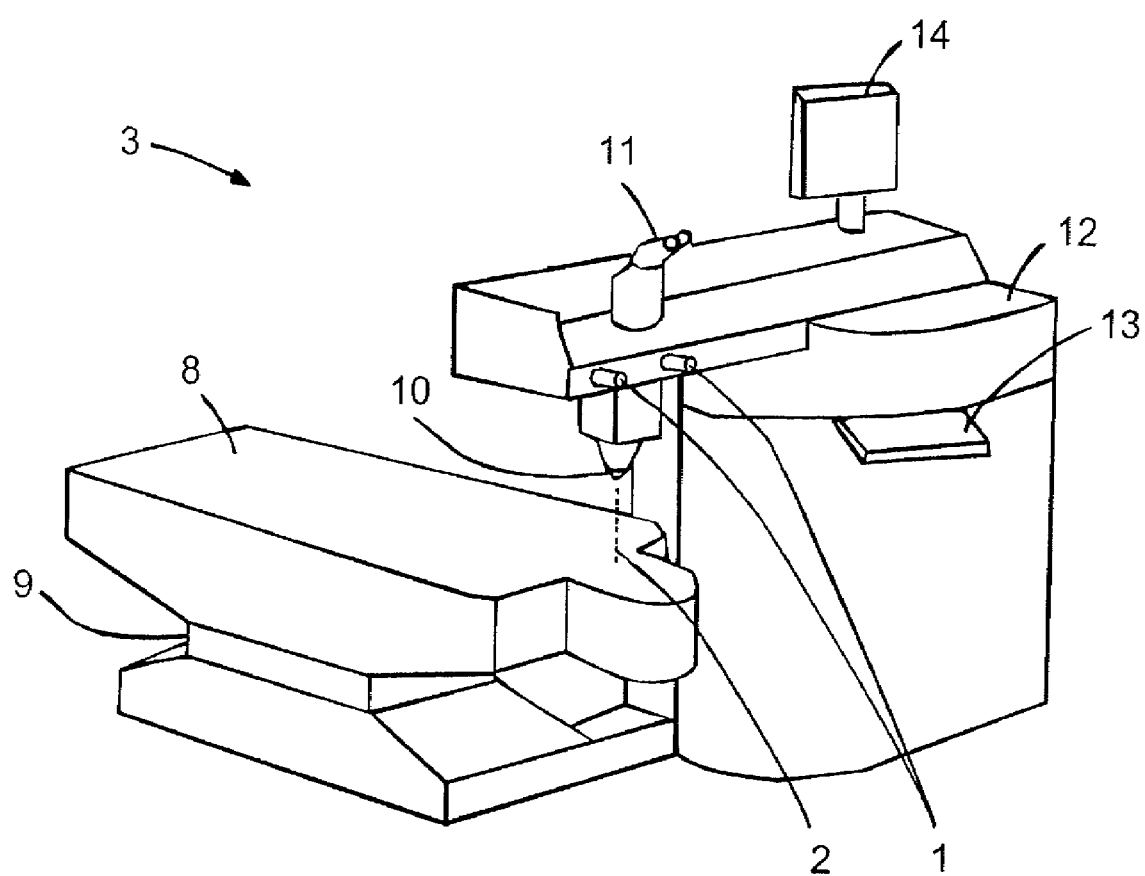
FIG. 3 is a perspective view of a refractive treatment device according to the invention featuring a femtosecond laser source.

FIG. 3 is a perspective view of the refractive treatment device according to this invention, 3, based on a laser source with a pulse duration in the femtosecond range and a pulse repetition frequency between 10 and 500 kHz. For instance, the refractive device, 3, used to correct ametropia, includes a resting unit for a patient (a gurney, 8) and a positioning device, 9, which supports the gurney, 8, and can move it in all three spatial dimensions. The gurney, 8, is aligned with the optical axis, 2, of the refractive treatment device, 3, when the patient is properly positioned. The refractive treatment device, 3, is also equipped with a treatment head, 10, which is located above the gurney, 8, as well as a microscope, 11, whereby the surgeon can observe the progress of the treatment. Furthermore, there is a computer, 12, with a keyboard, 13, and a monitor, 14. The positioning of the depicted two slit projector units, 1, shows that these are positioned at a large working distance from the eye of the patient, 4.

In another advantageous layout the slit projector units are designed to be able to be transported into a resting position while they are not being used. This resting position can, for example be (at least partially) inside the refractive treatment device.

With the solution according to this invention, a refractive treatment device is provided to allow follow-up examinations of the treated eye by means of integrated slit projection without the need for the patient to change positions. Thus, the examination can take place before, after or during the treatment, for example, if the treatment was interrupted.

Due to the additional two slit projector units the eye can be examined from different angles which significantly increases the reliability of the examination result.

To avoid unnecessarily restricting space and freedom of movement available to the patient and the operator, the two slit projector units are arranged and fixed, allowing a large working distance. In order to still achieve high precision when moving the projected slit image across the eye, the movement between the control element and the slit projector unit is regulated via a step-up gear unit. The available space and freedom of movement, especially for the operator, can be expanded even more if the slit projector units are designed to be moved into a resting position while not in use. This resting position may be inside the refractive treatment device.

Furthermore, the proposed intelligent lighting regimen facilitates the operation of the refractive treatment device significantly.

The invention claimed is:

1. A refractive treatment device, comprising:
   a slit projection system for examination of an eye of a patient wherein the slit illumination system comprises two slit projector units substantially symmetrically mounted at fixed angle of about 40° from the optical axis of the refractive treatment device and focused on the eye of the patient;
   the slit projector units each including a light source, a projection optical system, and beam forming and/or beam conducting optical components to project a slit image; and
   wherein at least one of the slit projector units further comprises a control unit adapted to precisely move the slit image across the eye to be examined.

2. The refractive treatment device as described in claim 1, wherein the slit projector units are positioned at a distance of about 200 to about 250 mm from the eye to be examined.

3. The refractive treatment device as described in claim 1, wherein the slit projector units comprise light source LEDs whose brightness is steplessly adjustable.

4. The refractive treatment device as described in claim 1, wherein warm white LEDs or white LEDs with switchable color filters are used to vary a color temperature of a light source of at least one of the slit projector units.

5. The refractive treatment device as described in claim 1, wherein at least one of the slit projector units comprises a generally cylindrical exterior.

6. The refractive treatment device as described in claim 1, wherein at least one of the slit projector units further comprises a coaxial planetary gear operably coupled with the control unit.

7. The refractive treatment device as described in claim 1, further comprising a control unit to regulate an intelligent lighting regimen operable so that a maximum of one slit projector unit or the treatment beam generated by a laser source of the refractive treatment device is operable at a time.

8. The refractive treatment device as described in claim 1, further comprising a femtosecond laser source to generate a treatment beam with pulse repetition frequencies between about 10 and about 500 kHz.

9. The refractive treatment device as described in claim 1, wherein the slit projector units are movable to a resting position while not in use.

10. The refractive treatment device as described in claim 9, wherein the resting position is at least partially inside the refractive treatment device.

11. A laser refractive treatment device to treat and examine an eye of a patient, comprising:
    a laser light source on an axis with the eye to be treated;
    a microscope; and
    two slit projector units that each generate a slit image substantially symmetrically fixedly mounted at an angle of about 40° from the optical axis of the refractive treatment device and focused on the eye of the patient,
    the slit projector units each including a light source, a projection optical system, and beam forming and/or beam conducting optical components;

wherein at least one of the slit projector units further comprises a control unit to precisely move the slit image across the eye to be examined.

12. The refractive treatment device as described in claim 11, wherein the slit projector units are positioned at a distance of about 200 to about 250 mm from the eye to be examined.

13. The refractive treatment device as described in claim 11, wherein at least one of the slit projector units comprises a light source comprising LEDs whose brightness is steplessly adjustable.

14. The refractive treatment device as described in claim 13, wherein the LEDs comprise warm white LEDs or white LEDs and further comprising switchable color filters that are used to vary a color temperature of a light source.

15. The refractive treatment device as described in claim 11, wherein at least one of the slit projector units further comprises a coaxial planetary gear operably coupled with the control unit.

16. The refractive treatment device as described in claim 11, further comprising a control unit operable so that a maximum of one slit projector unit or the treatment beam generated by a laser source of the refractive treatment device is illuminated at a time.

17. The refractive treatment device as described in claim 11, further comprising a femtosecond laser source to generate a treatment beam with pulse repetition frequencies between about 10 and about 500 kHz.

18. The refractive treatment device as described in claim 11, wherein the slit projector units are movable to a resting position while not in use.

* * * * *